(12) United States Patent
Gadberry et al.

(10) Patent No.: US 6,461,363 B1
(45) Date of Patent: Oct. 8, 2002

(54) SURGICAL CLIPS AND CLAMPS

(76) Inventors: Donald L. Gadberry, 33862 Mariana, Apt. B, Dana Point, CA (US) 92629; Nabil Hilal, 25291 Spindlewood, Laguna Niguel, CA (US) 92677; Todd Mrotek, 14701 Danberry Cir., Tustin, CA (US) 92780; Charles C. Hart, 8252 Mandeville, Huntington Beach, CA (US) 92646

( * ) Notice: Subject to any disclaimer, the term of this patent is extended or adjusted under 35 U.S.C. 154(b) by 0 days.

(21) Appl. No.: 09/381,123
(22) PCT Filed: Mar. 10, 1998
(86) PCT No.: PCT/US98/04702
§ 371 (c)(1),
(2), (4) Date: Aug. 22, 2000
(87) PCT Pub. No.: WO98/40020
PCT Pub. Date: Sep. 17, 1998

Related U.S. Application Data
(60) Provisional application No. 60/040,655, filed on Mar. 10, 1997.

(51) Int. Cl.[7] ............................................. A61B 17/10
(52) U.S. Cl. ........................................ 606/139; 606/142
(58) Field of Search ................................... 606/139, 142, 606/144, 147, 151

(56) References Cited

U.S. PATENT DOCUMENTS

| | | | | |
|---|---|---|---|---|
| 2,618,270 A | * | 11/1952 | Pearson | 606/139 |
| 4,058,126 A | * | 11/1977 | Leveen | 606/139 |
| 4,931,058 A | * | 6/1990 | Cooper | 606/158 |

* cited by examiner

*Primary Examiner*—Howard Weiss
*Assistant Examiner*—Hoa Trinh

(57) ABSTRACT

A surgical clamp includes a shaft having clamping jaws at a proximal end and an operative handle assembly at a distal end. The shaft has properties for being moved to a desired shape by the user prior to operation of the handle assembly and for holding the desired shape during operation of the handle assembly. The shaft may include a bendable element extending along an axis between the handle assembly and the jaws. A control element disposed relative to the bendable element is operable from the handle assembly at the proximal end of the shaft to move the jaws relative to each other at the distal end of the shaft. An associated method includes the step of bending the shaft to a desired shape prior to operation of the clamp and maintaining the shaft in substantially the desired shape during operation of the clamp.

22 Claims, 14 Drawing Sheets

FIG. I

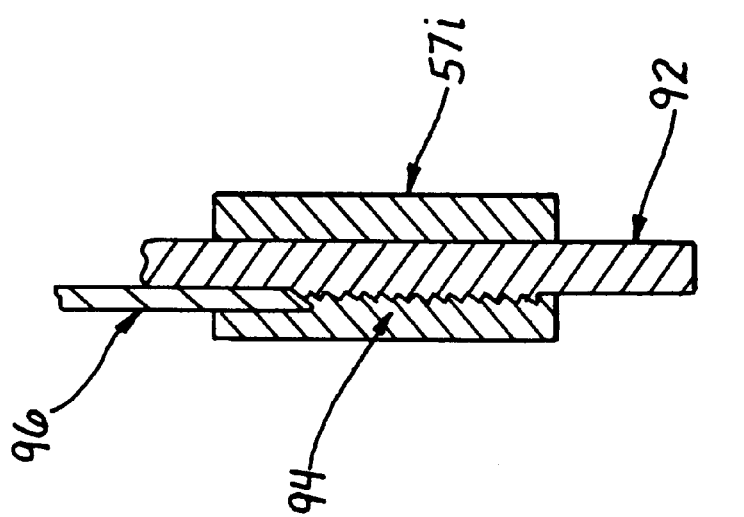
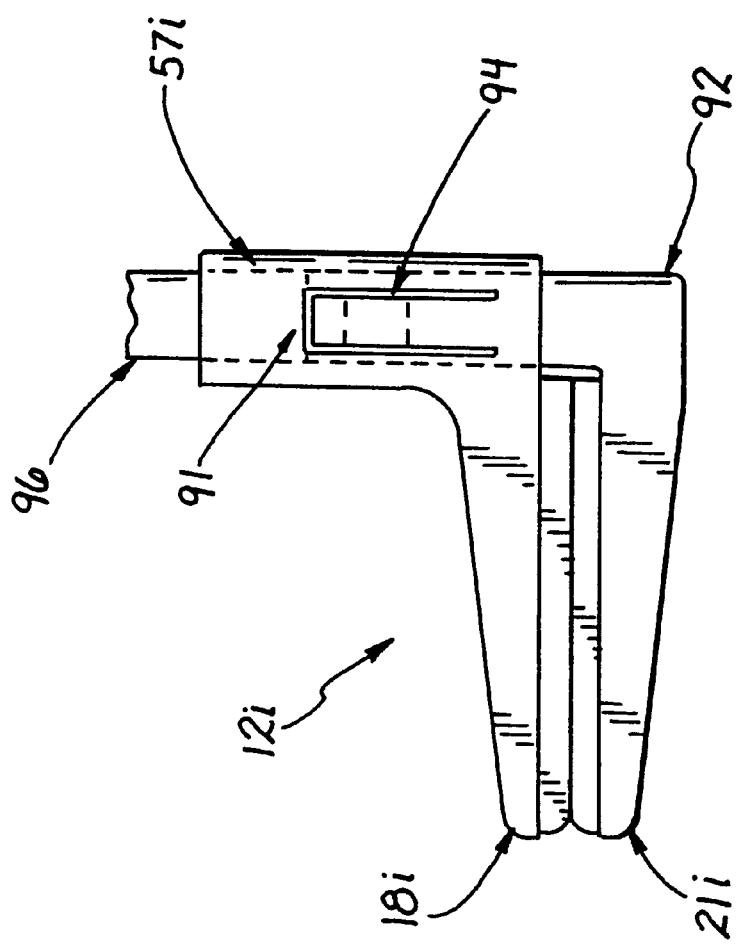

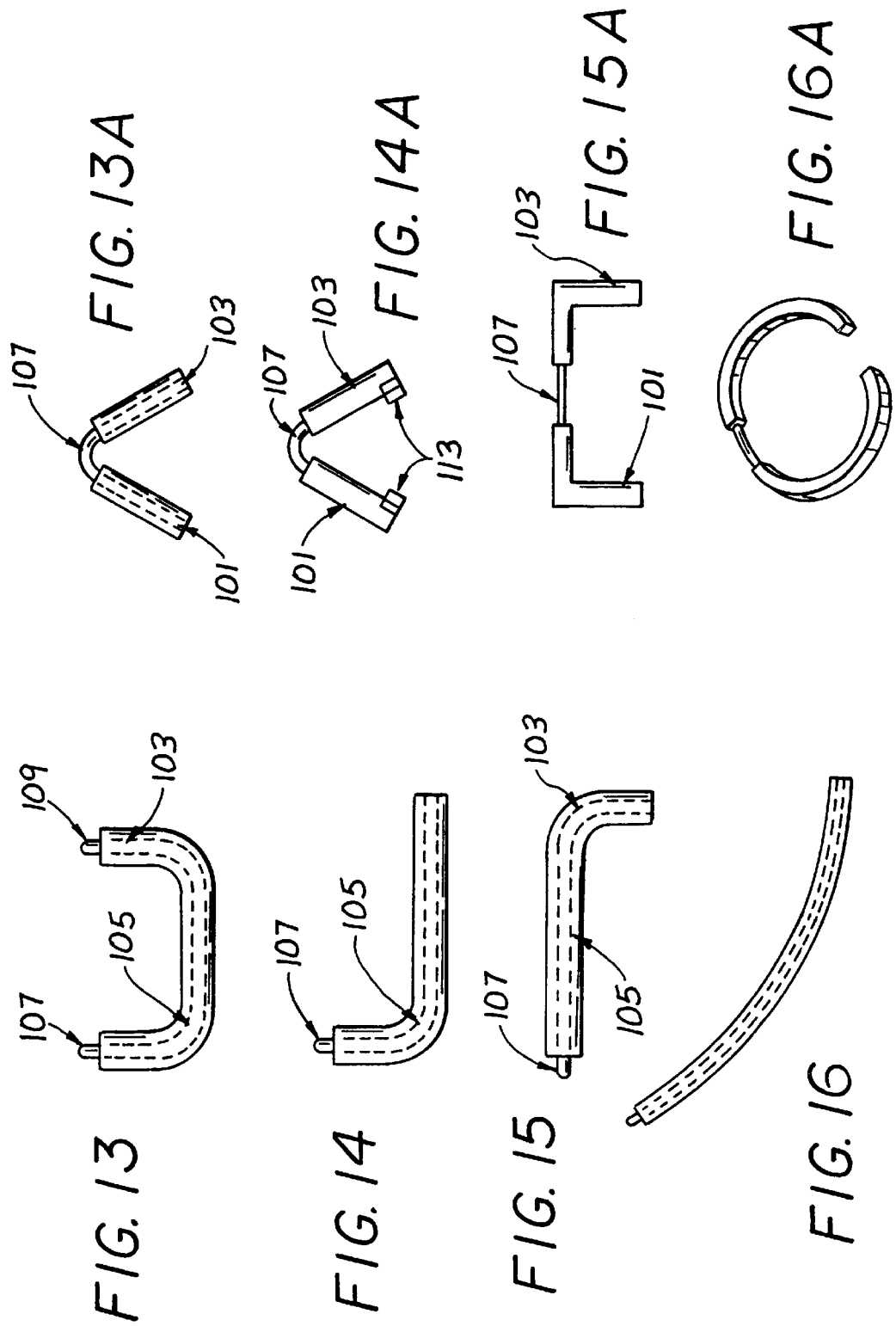

SURGICAL CLIPS AND CLAMPS

This application is a 371 of PCT/US98/04702 filed on Mar. 10, 1997 which claims benefit of provisional application No. 60/040,655, filed Mar. 10, 1997.

BACKGROUND OF THE INVENTION

1. Field of the Invention

This invention relates generally to clamps and more specifically to clips, clamps, and devices for operating same in a surgical environment.

2. Discussion of the Prior Art

Clamps have long been used to dilate and occlude body conduits, such as vessels, by pinching the conduit between opposing jaws. Inserts providing soft and tactile surfaces on the jaws have also been contemplated. In addition, coil springs have been used to maintain a closing force on the opposing jaws. Some clamps have been provided with an elongate configuration usually in the form of a shaft extending between the jaws and a handle which operates the jaws through the shaft. The shaft has typically been formed as a rigid, typically-straight assembly, which merely allows the user to reach deeply into a surgical cavity while operating the jaws exteriorly of the cavity. In some cases where the reach is desirable, the shafts of the elongate clamps have been provided with a floppy configuration facilitating use of the clamps along a circuitous path. These floppy shafts have permitted the jaws to be placed, but have isolated the jaws from incidental movement of the handle assembly. However, they have not been capable of holding a shaped configuration.

Neither the rigid, nor floppy structures of the prior art have addressed the need for an elongate clamp having a shaft that is semi-rigid, that is bendable to a desired shape prior to placement of the clamp and yet capable of maintaining that desired shape during placement and operation of the clamp. These semi-rigid characteristics are particularly desirable for reaching an object along a circuitous path. A fixed, curved shaft is not adjustable, and a floppy shaft is not capable of maintaining a bend during placement and operation of the clamp.

In some situations it is desirable to have a greater degree of control over the closing force in order to avoid trauma to the conduit. Greater control over other aspects of the placement, operation, maintenance, and removal of the clips and clamps is always of interest.

SUMMARY OF THE INVENTION

Various embodiments of clips and clamps are included within the scope of the present invention. These embodimentg not only include the operative members, including opposing jaws, but also various handles, ratchet systems, quick disconnect apparatus, and remote controls, which greatly facilitate control and operation of these systems. It will be clear that many of these system elements will be interchangeable with other elements in order to achieve a desired configuration and control.

At least one of the embodiments of the invention has an elongate configuration resulting primarily from a shaft which extends between the jaws of the clamp at a distal end of the shaft and a handle assembly at the proximal end of the shaft. The shaft in this case has a semi-rigid configuration so that it is initially bendable and yet capable of maintaining a bend during placement and operation of the clamp. The haft of the clamp may be corrugated or may be formed as a series of ball-and-socket elements. However, in most cases, the shaft will include a stationary element fixed between the housing and the jaws and a movable element movable by operation of the handle assembly to operate the jaws. Either of the fixed or movable elements may have the configuration of a tube in which case the other element is typically disposed within the tube.

The stationary element will typically be formed of a material that is malleable or otherwise semi-rigid. This permits the shaft and the clamp to be bent into a desired shape and yet to have sufficient rigidity to maintain that desired shape during placement of the clamp. In accordance with one aspect of the invention, the shaft has properties for being bent into a desired shape by the user prior to operation of the handle assembly and for holding the desired shape during operation of the handle assembly.

In another aspect of the invention, the shaft comprises a bendable element extending along a first axis between the handle assembly and the jaws. A control element extends relative to the bendable element along a second axis, the control element being operable from the handle assembly at the proximal end of the shaft to move the jaws relative to each other at the distal end of the shaft.

In a further aspect of the invention, operation of the clamp includes the step of bending the shaft to a desired shape prior to the surgical operation and maintaining the shaft in substantially the desired shape during the surgical operation. These and other features and advantages of the invention will be more apparent from a description of preferred embodiments in reference to the associated drawings.

DESCRIPTION OF THE DRAWINGS

FIG. 9 is a side elevation view of a clamp having an integral ratchet pawl;

FIG. 9A is an axial cross-section view of the clamp illustrated in FIG. 9;

FIG. 13 is a top plan view of a clip having two hinges and opposing jaws in Uconfiguration;

FIG. 13A is a side elevation view of the clip illustration in FIG. 13;

FIG. 14 is a top plan view of a clip with opposing jaws in a L-shaped configuration;

FIG. 14A is a side elevation view of the clip illustrated in FIG. 14;

FIG. 15 is a top plan view of an additional embodiment of a clip with aL-shaped configuration;

FIG. 15A is a side elevation view of the clip illustrated in FIG. 15;

FIG. 16 is a top plan view of a clip with a C-shaped configuration;

FIG. 16A is a side elevation view of the clip illustrated in FIG. 16;

FIGS. 20–22 show various steps in a method for shaping the cable of the clamp;

FIG. 20 is a perspective view showing the cable in a straight configuration;

FIG. 21 is a perspective view illustrating the cable being shaped to a predetermined configuration;

FIG. 22 is a perspective illustrating the properties of the cable which permit it to maintain the predetermined configuration while reaching into an operative site;

DESCRIPTION OF PREFERRED EMBODIMENTS

Figure 1:
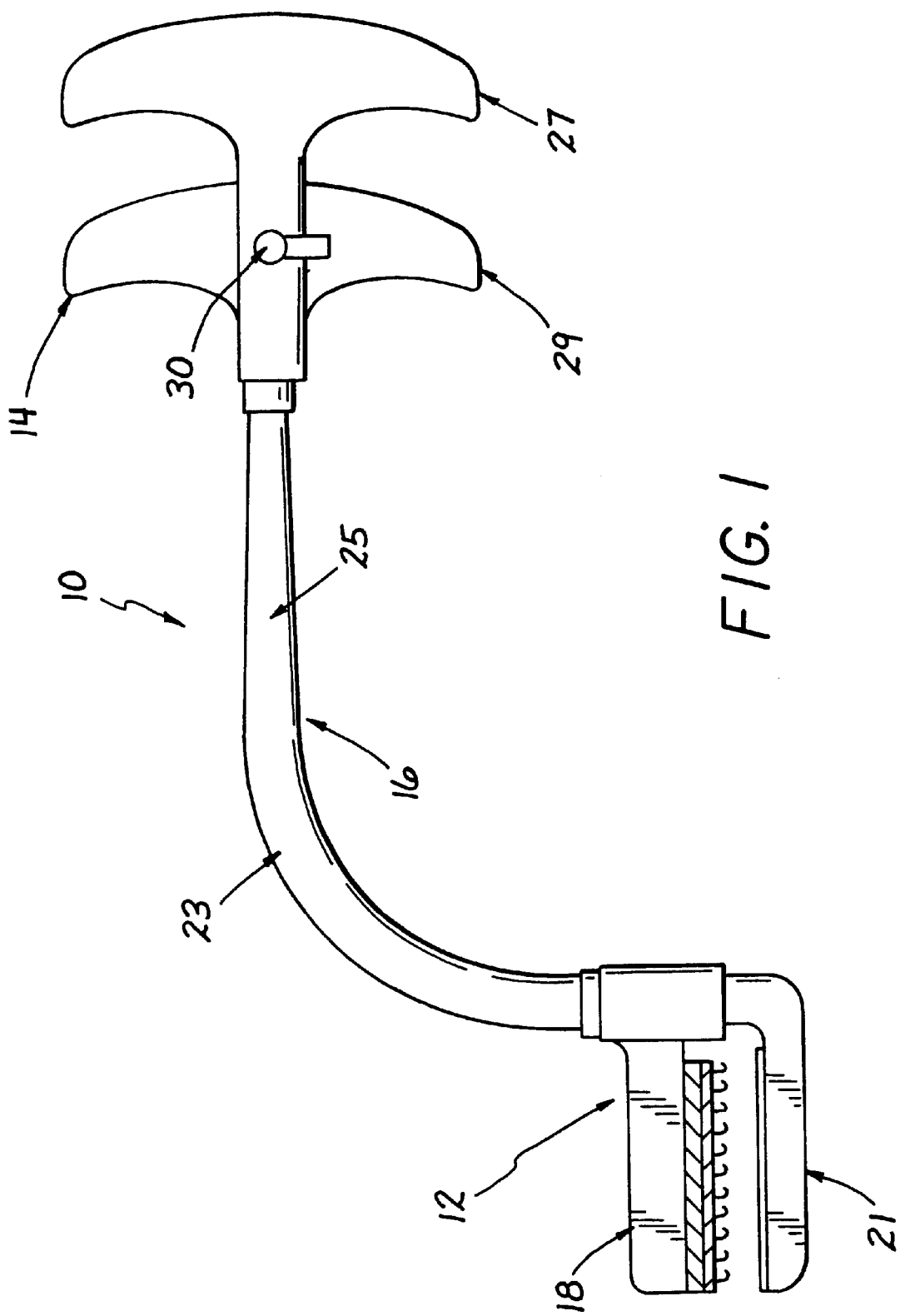
FIG. 1 is a side view of a clamp system including a T-handle assembly for remotely operating a parallel jaw clamp through a flexible cable in one embodiment of the invention.

A clamp assembly is illustrated in FIG. 1 and designated generally by the reference numeral 10. Included in the assembly are a clamp 12 and ahandle 14 connected by a shaft 16. In this embodiment, the clamp 12 has a pair of opposing parallel jaws 18 and 21 with a straight configuration. The cable 16 includes an outer jacket 23 and an inner cable 25 that are moveable relative to each other. The jacket 23 is attached to one of the jaws, such as the jaw 18 while the cable 25 is attached to the other jaw, such as the jaw 21. Thus, movement of the cable 25 relative to the jacket 23 causes the jaws 18 and 21 to move relative to each other.

The handle 14 in this embodiment includes a T-handle 27 that is adapted to rest in the palm of the user, and a T-bar 29 that is moveable relative to the T-handle 27. The T-handle 27 can be fixed to the jacket 23 while the T-bar 29 is fixed to the cable 25. Thus, operation of the T-bar 29 relative to the T-handle 27 moves the cable 25 relative to the jacket 23 and also moves the jaw I1 relative to the jaw 18.

Of particular interest in this embodiment is the remote location of the handle 14 relative to the clamp 12. Also, the cable 25 and associated jacket 23 can be flexible permitting movement of the handle 14 even after the clamp 12 has been operatively fixed in position.

Quick disconnects can be provided at opposite ends of the cable 16 and a ratchet mechanism can be provided in the handle 14 in order to maintain a predetermined space and pressure between the jaws 18 and 21. A lock lever 30 can be provided on the handle 14 to engage and release the ratchet mechanism.

Figure 2:
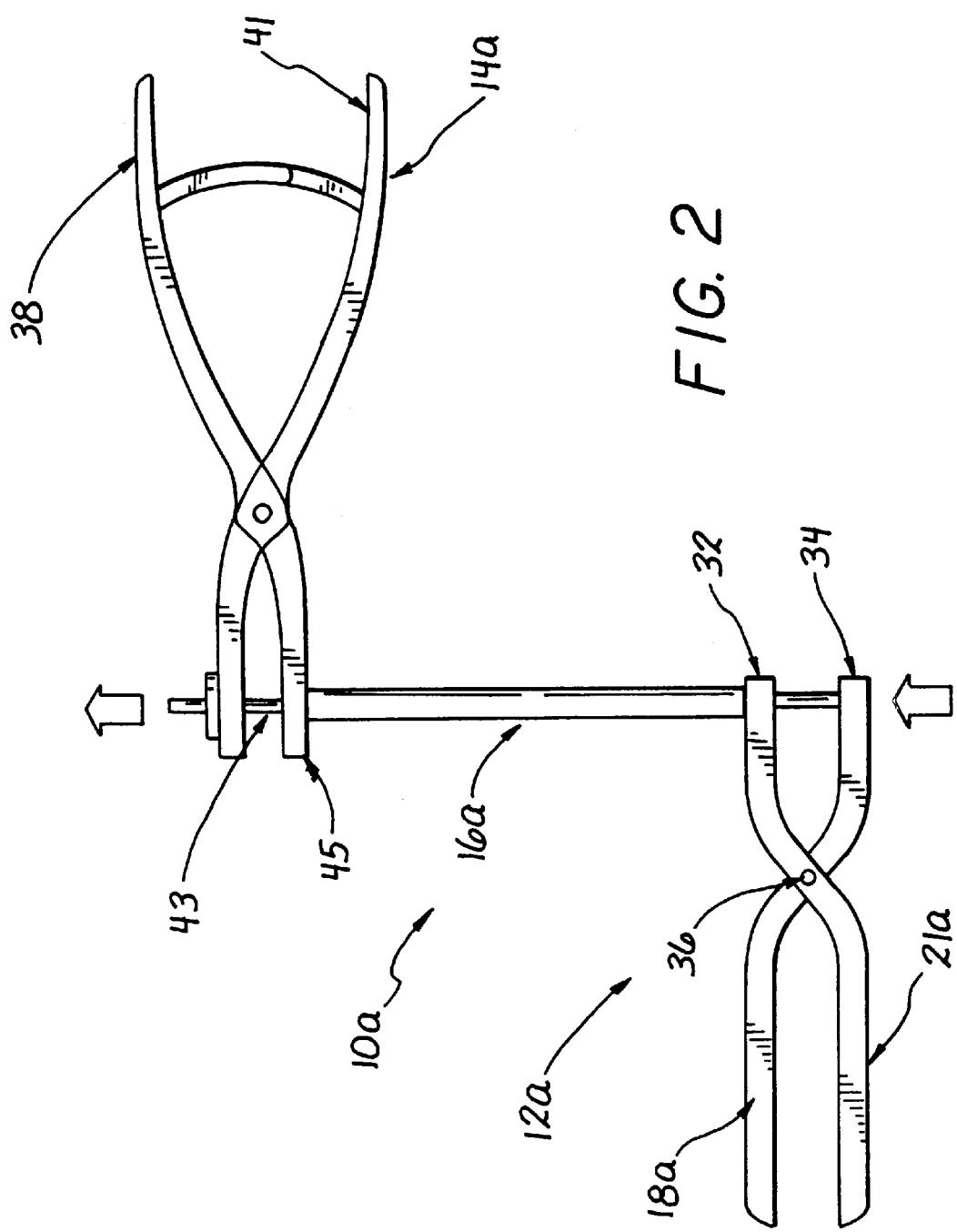
FIG. 2 is a side elevation view of a scissors clamp remotely operable by a scissors handle assembly.

A further embodiment of the clamp assembly is illustrated in FIG. 2. In this embodiment structural elements which are similar to those previously discussed will be designated by the same reference numeral followed by the lower case letter "a." Thus the clamping assembly 10a includes a clamp 12a, a handle 14a and a shaft 16a. In this case, the clamp 12a includes opposing jaws 18a and 21a, but these jaws are formed in a scissors configuration with opposing levers 32 and 34 disposed on opposite sides of a fulcrum 36. The shaft 16a can be either rigid or flexible as in the embodiment of FIG. 1. The handle 14a can also be provided with a scissors configuration with opposing palm and finger grips 38 and 41, respectively, and associated jaws 43 and 45.

The jaws 43 and 45 are connected to an associated one of the cable and jacket of the shaft 16a. In this manner, movement of the grips 48 and 41 produces relative movement between the cable and jacket of the shaft 16a as well as the jaws 18a and 21a of the clamp 12a. It will be noted that the jaws 43 and 45 of the handle 14a can be a formed integral with different ones of the grips 38 and 41 so that closure of these grips can alternatively result in either opening or closing the jaws 18a and 21a.

Figure 3:
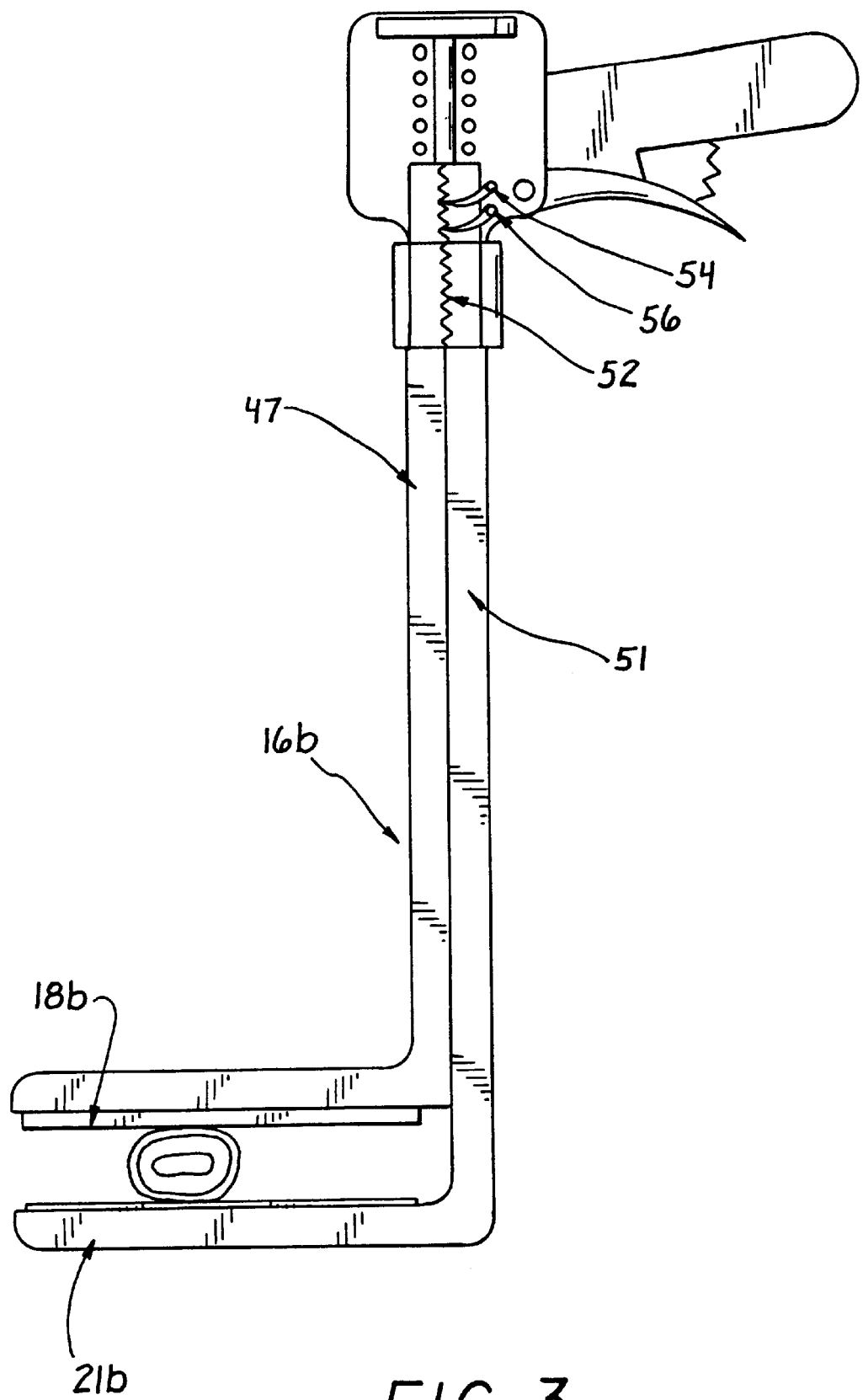
FIG. 3 is a further embodiment of a clamp system including a handle assemble with a 2-pawl mechanism.

A further embodiment of the invention is illustrated in FIG. 3 where elements of similar structure are designated by the same reference numeral followed by the lower case letter "b." In this embodiment, the shaft 16 of previous embodiments is formed as two shafts 47 and 51 that are axially moveable relative to each other. The jaws 18b and 21b are attached to associated ones of these shafts 47 and 51. The handle 14b in this embodiment also includes a ratchet mechanism including a ratchet gear 52 attached to the shaft 47, and a pair of pawls 54 and 56 which are independently pivotal on the shaft 51 to engage the ratchet gear 52.

Figure 4:
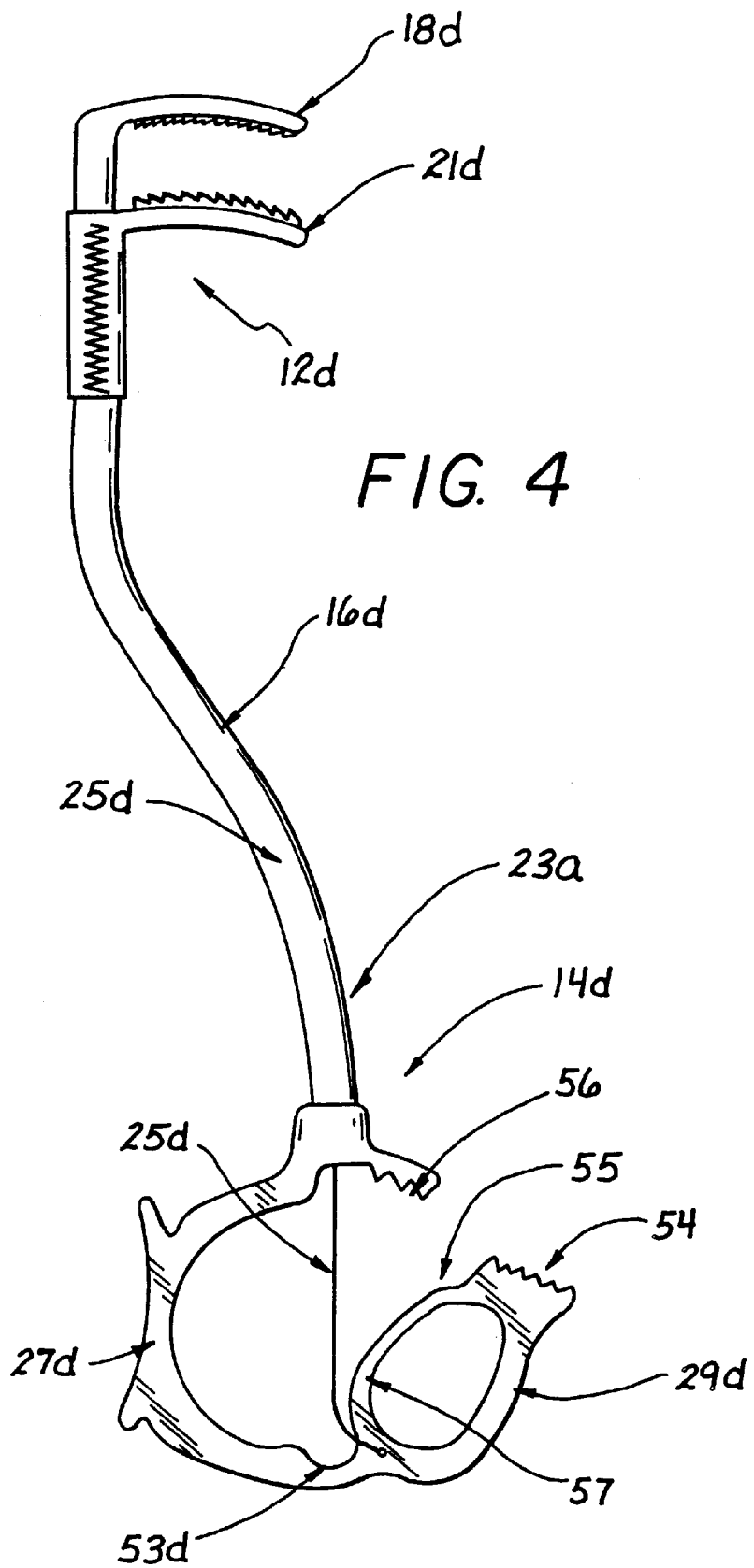
FIG. 4 is a side elevation view of a clamp system including a clamp having rounded jaws and an actuation handle providing for variations in force and speed of closure.

A further embodiment of the invention is illustrated in FIG. 4 where elements of similar structure are designated by the same referenced numeral followed by the lower case letter "d." The shaft 16d of this embodiment is similar to that illustrated in FIG. 1 as it includes a jacket 23d and coaxial cable 25d. In this embodiment, the jaws 18d and 21d of the clamp 12d are parallel but provided with a curved rather than a straight configuration. Also, inserts are illustrated for these jaws 18d and 21d. These inserts can be provided with a "sawtooth" pattern to facilitate atraumatic gripping of a vessel.

The handle 14d of this embodiment is of particular interest. It includes opposing grip portions 27d and 29d that are molded with a living hinge 53 therebetween. This hinge 53d forms a fulcrum for this lever system. The cable 25d is attached near the hinge 53 preferably to the grip 29d.

The finger grip 29d is provided with a camming surface 55 which rides against the cable 25d. As the grips 27d and 29d are moved into proximity, the cable 25d is forced against the camming surface 55 and thereby moved relative to the jacket 23d of the shaft 16d. The camming surface 55 can be provided with a circular configuration, as in the illustrated environment, or with any other configuration to facilitate variations in speed, distance and force applied to the cable 25d.

A ratchet mechanism can also be provided in this embodiment. In this case, a ratchet gear 54 and pawl 56 can be formed on engaging surfaces of the grip members 29d and 27d, Grespectively. It will be noted that in this embodiment that the camming surface 55 can be formed on a thin, flexible member 57 in order to provide some "give" to the cable 29b as the gripping members 27d and 29d are moved into proximity.

Figures 5, 5A:
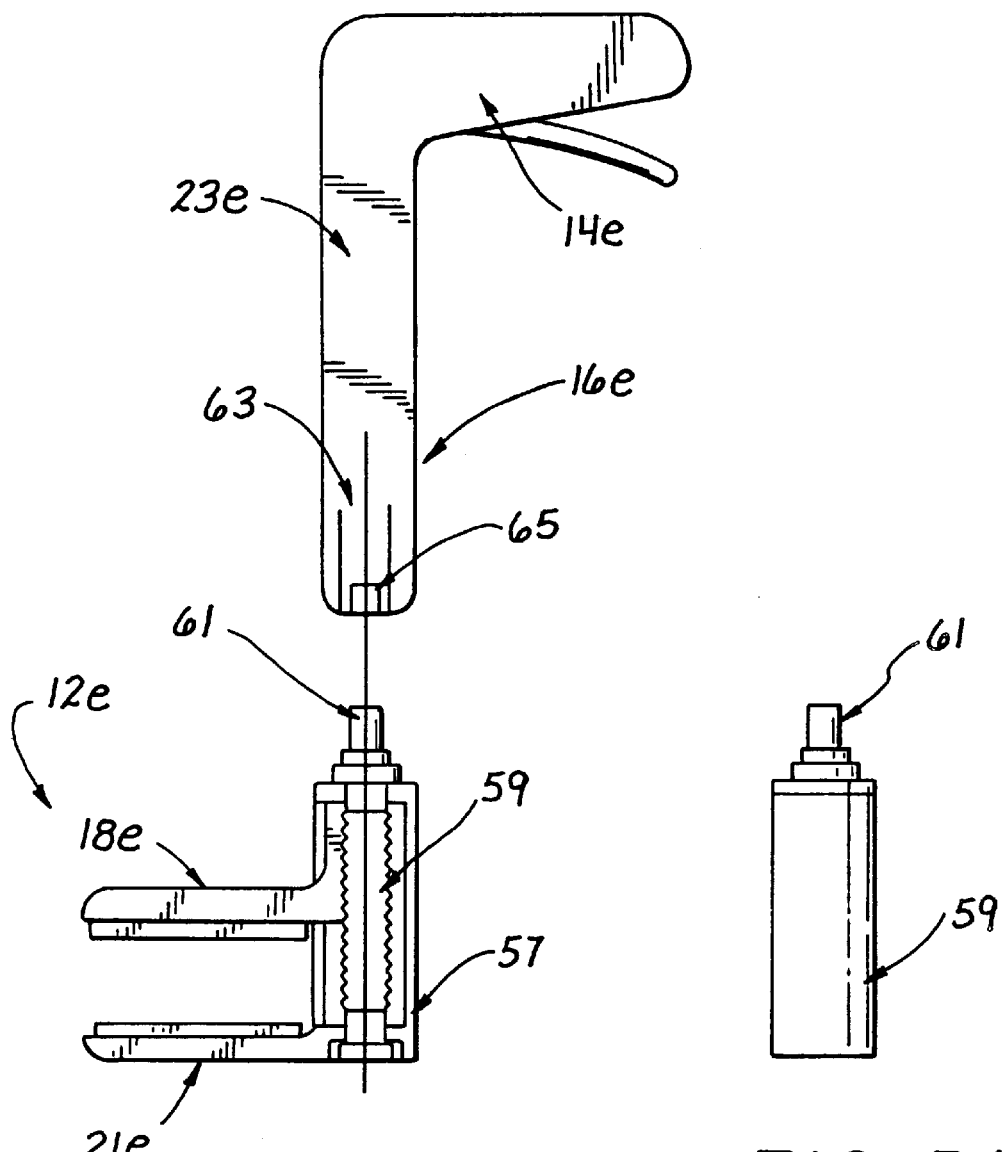
FIG. 5 is a side elevation view of a further embodiment including a handle assembly and shaft detachable from a clamp.
FIG. 5A is a rear elevation view of the clamp illustrated in FIG. 5.

An additional embodiment of the invention is illustrated in FIG. 5 wherein elements of similar structure are designated by the same reference numeral followed by the lower case letter "e." In this embodiment, the lower jaw 21e of the clamp 12e is formed integral with a cylindrical housing 57 which is slotted to receive the upper jaw 18e. A screw 59 extends through the housing 57 where its thread engages the upper jaw 18e. As the screw 59 turns, the upper jaw 18e rides on the threads of the screw 59 and thereby moves relative to the fixed jaw 29e and housing 57.

The screw 59 is provided with a stub 61 at its proximal end, the stub 61 having in radial cross-section a shape which is non-circular, such as square. This stub 61 is adapted for removable engagement by an associated handle 14e and shaft 16e mechanism. In this case, the shaft 16e includes a rigid jacket 23e and an associated rigid coaxial shaft 63. Operation of the handle 14e in this embodiment results in rotating the inner shaft 63 relative to the jacket 23e. A recess 65 at the distal end of the shaft 63e can be shaped complimentary to the stub 61 of the clamp 12e to provide a mating engagement between these elements. Then, as the handle 14e is operated, the shaft 63 turns along with the stub 61, and the jaws 18e and 21e move relative to each other, The ease with which the clamp 12e and shaft 16e can be engaged and disengaged is a significant feature of this embodiment.

Figure 6:
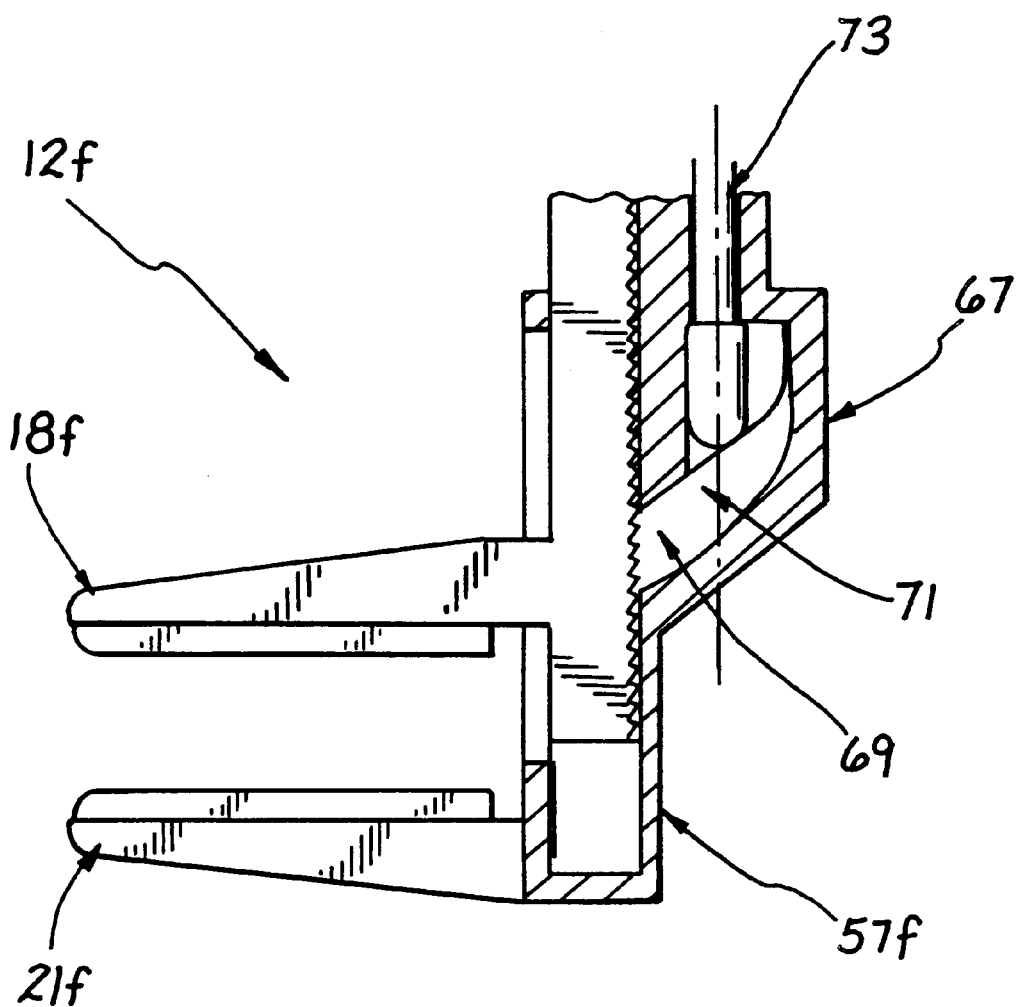
FIG. 6 is a side elevation view of a clamp interchangeable with the foregoing handle assemblies.

An alternative clamp is illustrated in the embodiment of FIG. 6 where elements of similar structure are designated by the same reference numeral followed by the lower case letter "f." In this embodiment a pawl mechanism 67 is provided on the clip 12f. This mechanism 67 includes a ratchet gear 69 formed on the jaw 18f, and a pawl formed on the housing 57f associated with the lower jaw 21f. As the jaw 18f moves relative to the jaw 21f, the ratchet gear 69 moves relative to the pawl 71 with a racketing action well known in the art. A pin 73 can be provided on the housing 57f to release the pawl 71 from engagement with a ratchet gear 69. By providing the pawl mechanism 67 on the clamp 12f, a higher degree of ratchet control can be provided in proximity to the jaws 18f and 21f.

Figure 7:
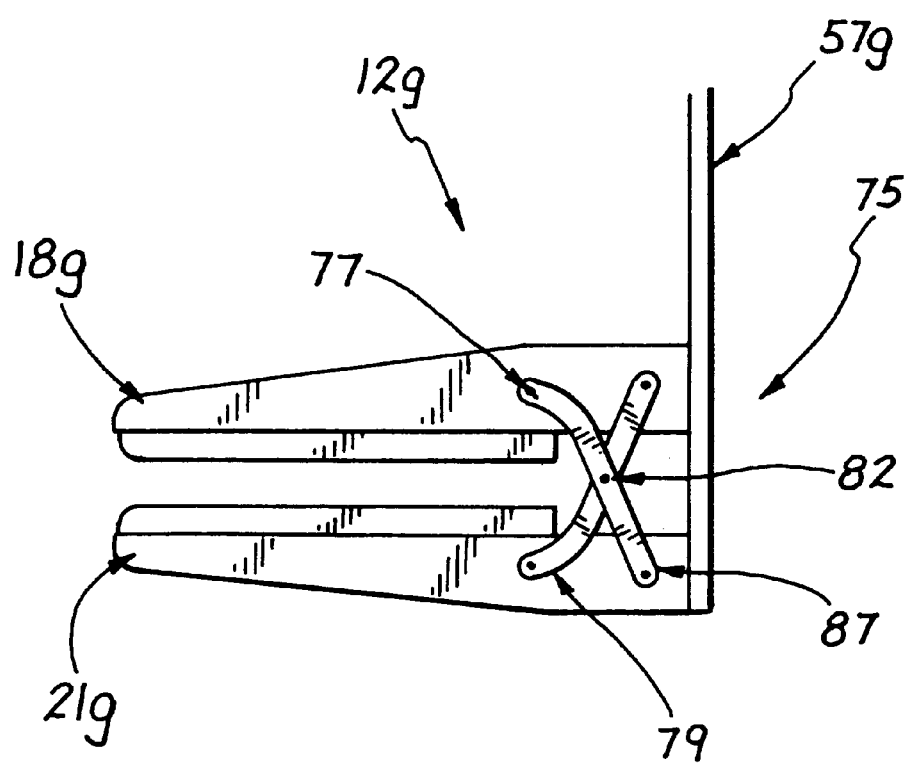
FIG. 7 is a side elevation view of a further clamp operable with the handle assemblies noted above.

A further clamp mechanism is illustrated in FIG. 7 wherein elements of similar structure are designated by the same reference numeral followed by the lower case letter "g." In this case, the jaws 18g and 21g are provided with a scissors mechanism 75 which tends to maintain the jaws 18g and 21g in a parallel orientation. A mechanism 75 has a scissors configuration with opposing elements 77 and 79 pivotal on one of the jaws 18g and 21g and slidable in a groove on the other of the jaws 18g and 21g. A pin 82 joins the scissors element 77 and 79 to provide a fulcrum. Movement of this pin 82 relative to the housing 57g causes the jaws 18g and 21g to open and close. Of course the clamp 12g can be operated in other manners, for example by moving the jaw 18g, or either of the scissors elements 77 and 79 relative to the housing 57g.

Figure 8:
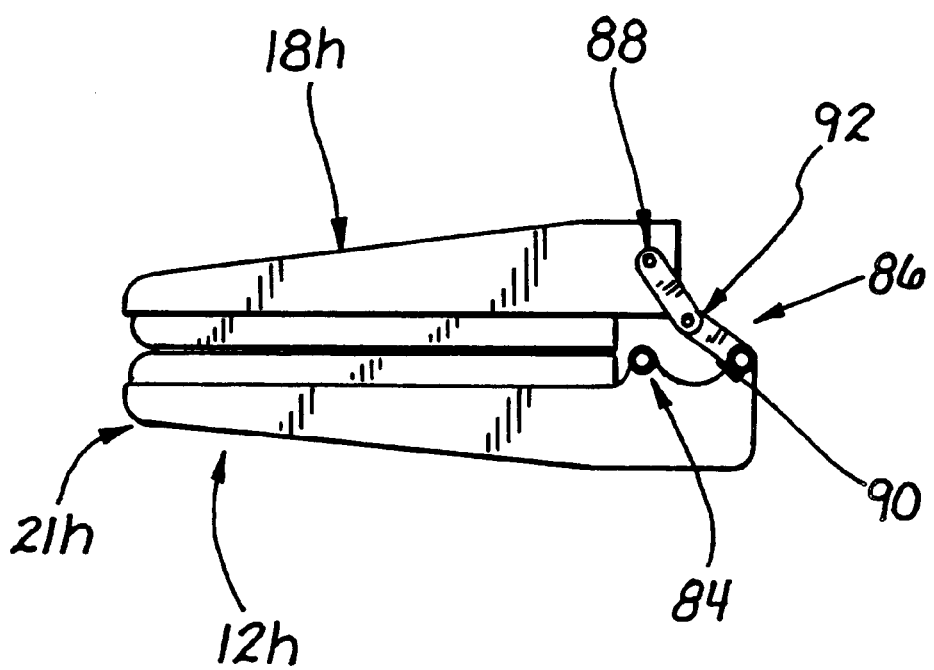
FIG. 8 is a side elevation view of a clamp having an overcenter mechanism.

In the embodiment of FIG. 8, elements similar to those previously described are designated by the same reference numeral followed by the lower case letter "h." In this embodiment, the jaws 18h and 21h may not move parallel to each other. These jaws 18h and 21h are joined at a pivot pin 84 and are also joined by an overcenter mechanism designated by the reference numeral 86. This mechanism 86 includes a leg 88 pivotal on the jaw 18h and a leg 90 pivotal on the jaw 21h. These legs 88 and 90 are joined by a fulcrum pin 92 to form an overcenter mechanism which facilitates releasable locking engagement of the jaws 18h and 21h. Actuation of this clamp 12h can be accomplished by engaging the fulcrum pin 92 and moving it relative to the jaw 21h to open and close the jaw 18h.

Elements similar to those previously described are designated by the same reference numeral followed by the lower case letter "i", in a further embodiment illustrated in FIG. 9. In this embodiment, the clamp 12i includes an upper jaw 18i which is integral with the housing 57i. The lower jaw 21i extends through this housing 57i for operation by the shaft 92 and housing assemblies. The ratchet gear 91 is formed on this shaft 92 while a ratchet pawl 94 is molded into the housing 57i. A ratchet release 96 can be slidable along the shaft 92 to separate the pawl 94 from the ratchet gear 91.

Figure 10:
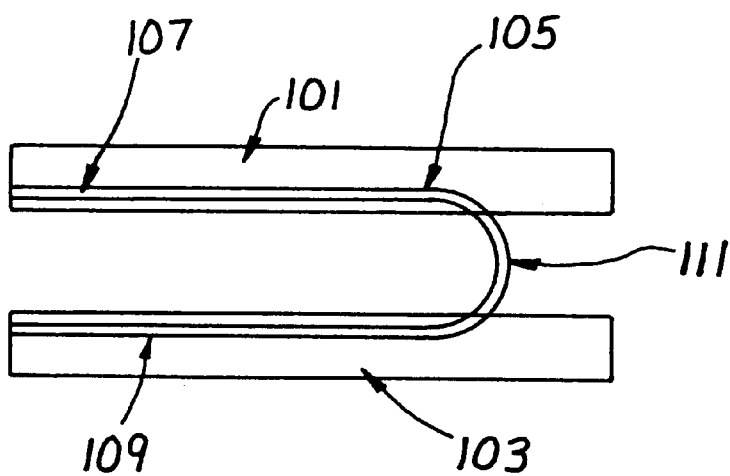
FIG. 10 is a side elevation view of a clip having a rounded spring and operable by a lever mechanism.
Figure 11:
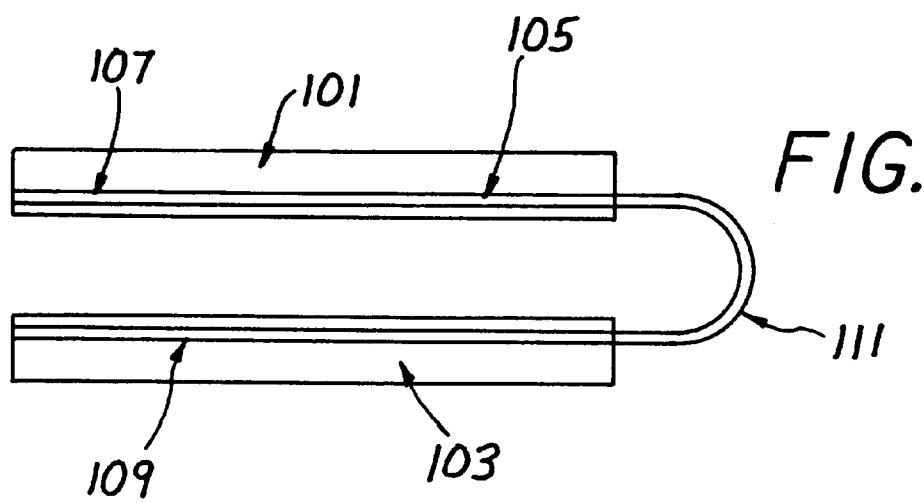
FIG. 11 is a flrther embodiment of spring clip of the present invention.
Figure 12:
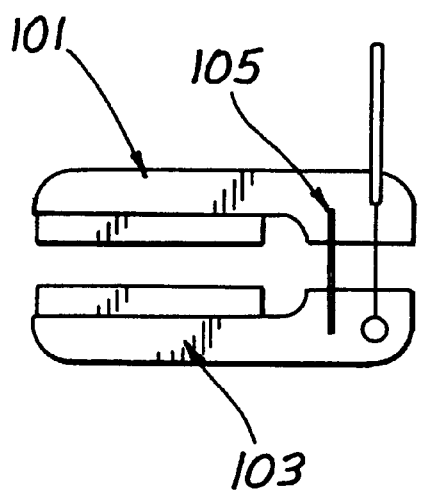
FIG. 12 is a side elevation view of a further embodiment of a clip with a straight spring.

FIGS. 10–12 relate to clip designs that are particularly adapted for occluding vessels. Each of these clips includes a pair of opposing jaws 101 and 103. A wire form hinge 105 is connected to these jaws 101 and 103 and biases them to a closed, occluding relationship. In the embodiment of FIGS. 10 and 11, the wire hinge 105 is bent back on itself to form opposing legs which are disposed to extend along the jaws 101 and 103, respectively. In the embodiment of FIG. 10, a closed end 111 of the hinge 105 is positioned intermediate the ends of the respective jaws 101 and 103. In this embodiment, the closed end 111 functions as a fulcrum. A force applied to that portion of the jaws 107 and 109 which extend beyond the end 111 opens the jaws 101, 103 of the clip.

This operation can be compared with the clip disclosed in FIG. 11 where the closed end 111 of the wire hinge 105 extends beyond the length of the jaws 101 and 103. Although the hinge 105 provides the same bias for the jaws 101, 103 as in the embodiment of FIG. 10, actuation of this structure requires an opposing force against the arms 107, 109 of the hinge I05 or the jaws 101, 103 in order to open the clip.

A further embodiment of the clip is illustrated FIG. 12 where the wire hinge 105 has a straight configuration. This hinge of 105 could be provided either by a metal wire or a flat wire spring. In this case the hinge 105 extends generally perpendicular to the jaws 101 and 103. Nevertheless, it provides the same bias action to close the clip as in the embodiments of FIGS. 10 and 11. The placement of this hinge 105 in FIG. 12 will of course be between the ends of the respective jaws 101 and 103 so that the clip can be operated in the manner discussed with reference to FIG. 10.

Other embodiments of the clip of the present invention are illustrated in FIGS. 13–16 and the associated side views of FIGS. 13a–16a. In each of these embodiments, at least one wire hinge 105 is provided as in the foregoing embodiments. However, as opposed to the straight parallel jaws of FIGS. 10–12, the opposing jaws 103 and 105 in these embodiments are provided with other than a straight shape. Thus in the embodiment of FIGS. 13 and 13a, the jaws 101 and 103 have a U-shaped configuration. The wire hinge 105 extends throughout the length of these jaws 101 and 103 and forms two hinges 107 and 109 at these opposing ends.

The embodiment of FIGS. 14 in 14a includes jaws 101 and 103 which have an L-shaped configuration with the hinge 107 of the wire 105 formed at the end of the short leg of the jaws 101, 103. As illustrated in FIG. 14a, the free end of the L-shaped legs can be provided with an extension or "toe-in" 113 to compensate for spring action.

The embodiment of FIGS. 15 and 15a also have an L-shaped configuration. However, in this embodiment, the hinge 107 is formed at the end of the long leg of the "L".

In a further embodiment illustrated in FIG. 16 and 16a, the jaws 101 and 103 have a C-shaped configuration. In this embodiment, only one hinge 107 is illustrated although two hinges 107, 109 can be provided as in the embodiment of FIG. 13.

Figure 17:
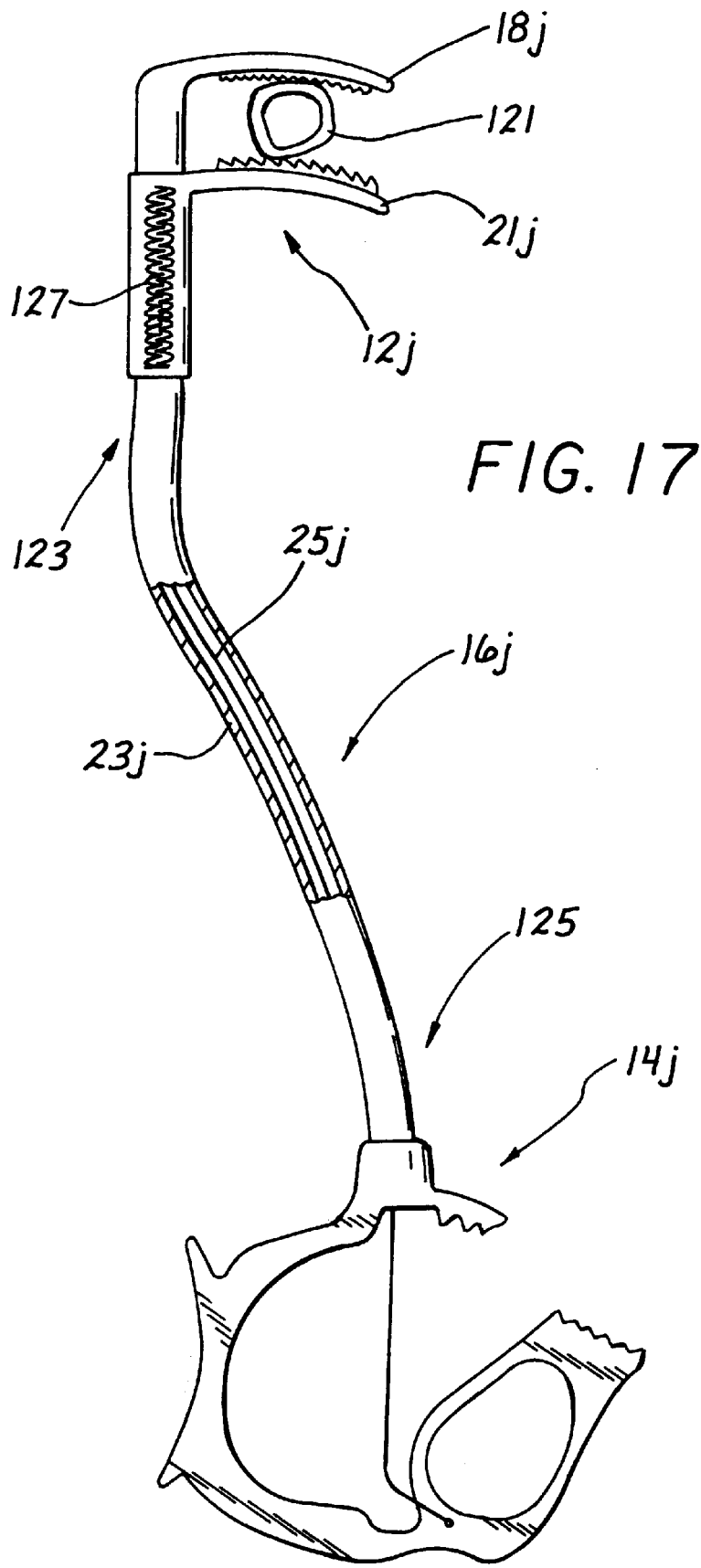
FIG. 17 is a side elevation view of the clamp system illustrated in FIG. 4 partially in cross-section to illustrate the ghapability of a cable assembly disposed between the clamp and the handle assembly.
Figure 18:
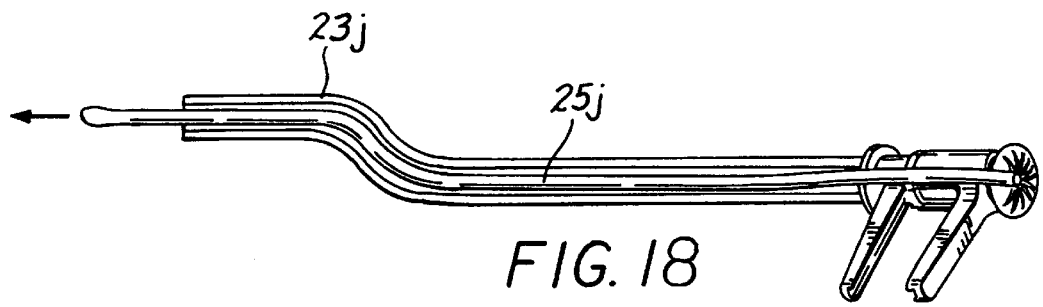
FIG. 18 is a perspective view partially in axial cross-section of an embodiment wherein the inner element is movable relative to an outer jacket.

FIG. 17 is a perspective view similar to that of FIG. 4. In this view, elements of structure similar to those previously disclosed will be designated with the same reference numeral followed by the lower-case letter j. Thus, the embodiment of FIGS. 4 and 17 includes the flexible cable assembly 16j, which is similar to the assembly 16d in that it is both flexible and shapable. In effect, the cable assembly 16j is semi-rigid so that it is not merely floppy and incapable of holding a shape, but rather bendable to a desired configuration. Once the assembly 16j has been bent to a predetermined shape, it is capable of maintaining that shape so that the clamp assembly 10 is adapted to reach into difficult locations to engage, grasp, and perhaps occlude an object such as a blood vessel 121. As previously noted, the cable 1 6j has a distal end 123 adapted to receive the clamp 12j, and a proximal end 125 adapted to receive the handle.

In the manner previously discussed, the cable 16j will typically include the jacket 23j and a co-axial cable or element 25j. One of the jacket 23j and the element 25j is fixed while the other of the jacket 23j and the element 25j is movable and attached to the other jaw 18j and 21j. For example, in the embodiments of FIGS. 4 and 17, the jacket 23j is fixed and attached to the jaw 21j while the element 25j is movable relative to the jacket 23j and attached to the jaw 18j. In this case, the jaws 18j and 21j are biased to an open position by a compression spring 127. As the handle 14; is operated, the element 25j is pulled proximally relative to the jacket 23i thereby opposing the bias of the compression spring 127 and moving the jaw 18j into a closing relationship with the jaw 21j.

This embodiment of FIGS. 4 and 17 is only one of several embodiments wherein the cable 16j is flexible so that it has properties for being adjusted to a predetermined shape and for maintaining that shape until further adjusted. These characteristics of the cable 16j are of particular advantage when it is desirable to engage or occlude an object, such as the blood vessel 121, that is not accessible in a straight line. By adjusting or bending the cable 16j, the clamp 12j can be moved around organs and otherwise directed along a circuitous path to engage the vessel 121. The clamp 12j can then be operated at the distal end 123 of the cable 16j by manipulating the handle 14j at the proximal end 125. These flexible characteristics are also referred to herein as semi-rigid properties. The cable 16j is preferably sufficiently soft that it can be shaped to a predetermined curved configuration, but also sufficiently rigid that it can maintain the predetermined configuration until it is re-shaped.

These properties of the cable 16j can be achieved by providing either the jacket 23j or the inner element 25j with the shapable characteristics. For example in FIG. 21, the clamp 12j is operable by moving the inner element 25j relative to the fixed outer jacket 23j. In the embodiment of FIG. 22, the outer jacket 23j is movable relative to the fixed inner element 25j.

Typically, but not necessarily, it is the stationary or fixed one of the jacket 23j and inner element 25j, that is provided with the shapable characteristics. The other of the jacket 23j and inner element 25j will typically not be shapable.

Figure 21:
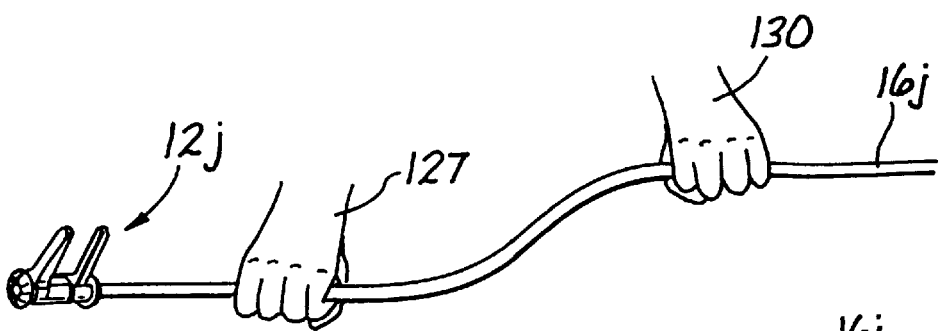
Figure 22:
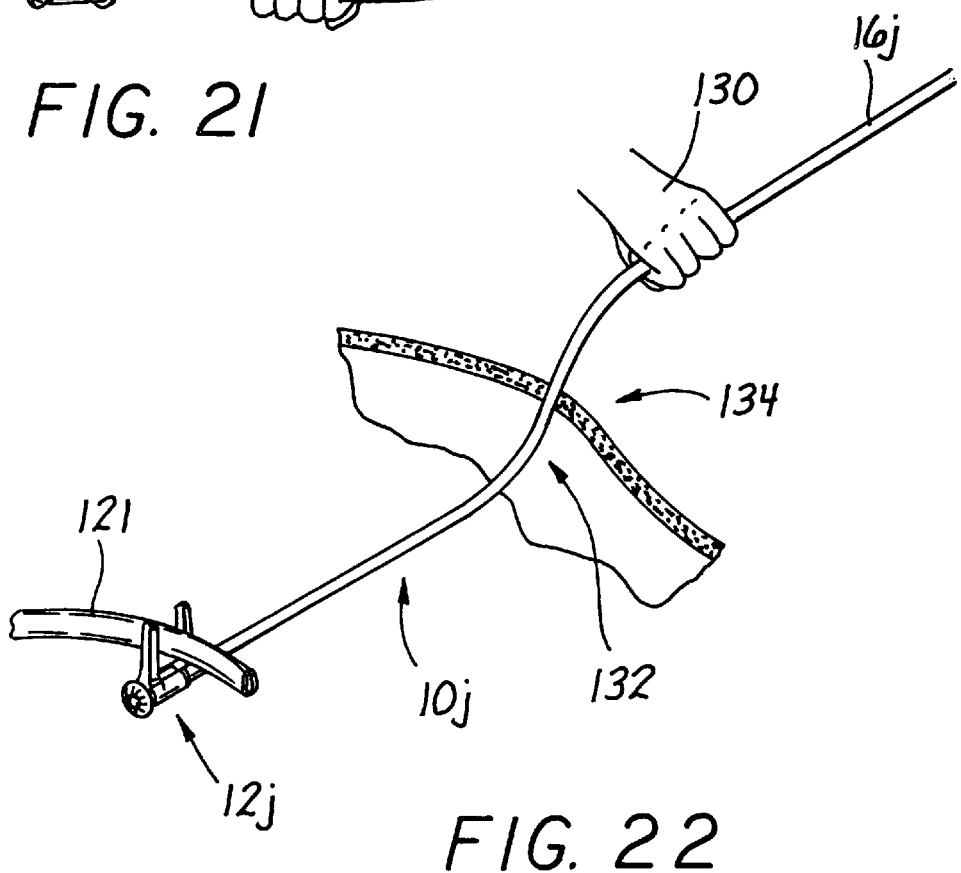

In operation, the movable element, such as the element 25j, follows the predetermined curve of the shapable element, such as the outer jacket 23j in FIG. 21. The movable element, such as the inner element 25j, will usually have tension characteristics to oppose the bias of the spring 127 and to move the clamp 12j into a closed state. In some embodiments, the jaws of the clamp 12j will not be biased in which case the movable element will typically have both tension and compression characteristics to move the jaws 18j and 21j into an closed position or open position, respectively.

Figure 19:
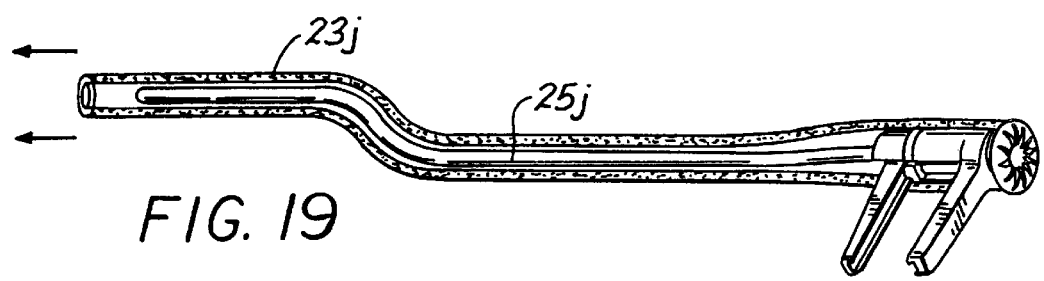
FIG. 19 is a perspective view partially in axial cross-section of an embodiment wherein the inner element is movable relative to the outer jacket.
Figure 20:
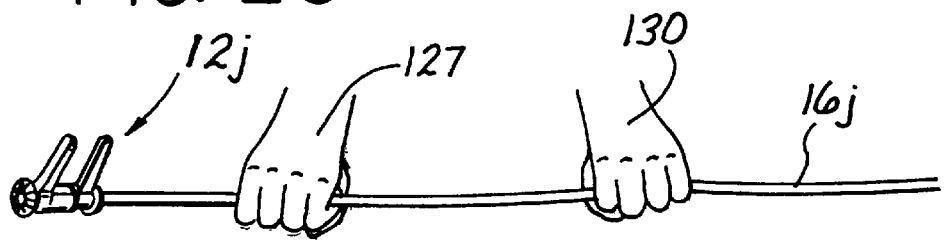
FIG. 20 is a perspective view partially in axial cross-section of an embodiment wherein the outer jacket is movable relative to the inner element.

The semi-rigid cable 16j will typically be provided in a straight configuration such as that illustrated in FIG. 20. The user will then bend the cable 16j to a predetermined shape using both hands 127, 130. The predetermined shape may include an S-curve as 132, as illustrated in FIG. 19. Importantly, the semi-rigid properties of the cable 16j enable it to maintain this predetermined shape, such as the S-curve 132 until it is re-shaped, typically by using both hands 127, 130. With these characteristics, the shapable clamp assembly 10j can be used to reach along a circuitous path in order to engage the blood vessel 121 at an operative site such as that designated by the referenced numeral 134 in FIG. 20.

Figure 23:
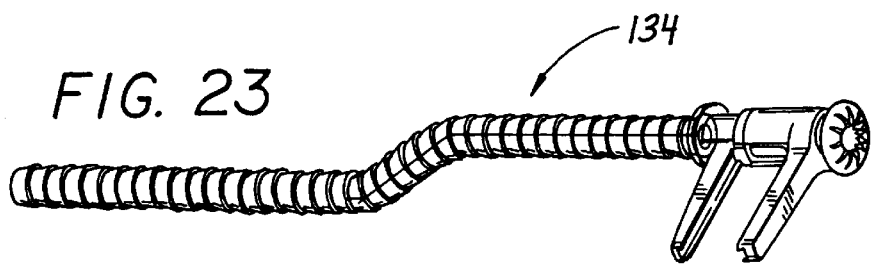
FIG. 23 is a perspective view illustrating the outerjacket of the cable provided in the form of a corrugated tube.
Figure 24:
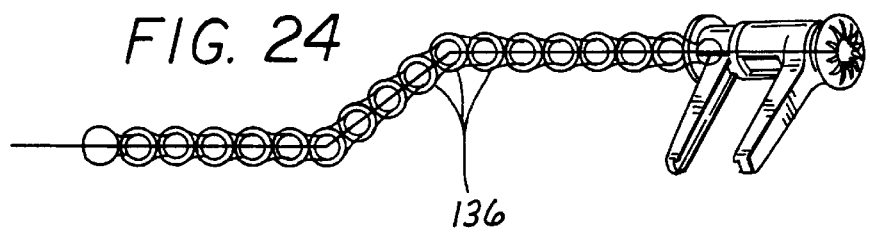
FIG. 24 is a perspective view illustrating the outer jacket of the cable provided in the form of a series of ball-and-socket joints.

The shapable characteristics of either the outer jacket 23j (in the case of the FIG. 22 embodiment) or the inner element 25j (in the case of the FIG. 21 embodiment) can result from several different structural configurations. For example, the fixed element, such as the outer jacket 23j, can be formed from a metal which is bendable or malleable to achieve the desired shape. The semi-rigid characteristics can also be facilitated by forming the outer jacket 23j in the shape of a corrugated tube 134 illustrated in FIG. 23. The semi-rigid, shapable characteristics can also be achieved by providing the outer jacket 23j in the form of a series of ball-and-socket joints 136 as illustrated in FIG. 24.

With reference to all of the foregoing embodiments, it will be apparent that many variations can be achieved by combining any of the clips or clamps with any of the handles or remote cable assemblies. In addition, the placement of ratchet assemblies can be varied. For example the ratchet assembly can be provided in the handle assembly as illustrated in FIG. 3, or in the clamp assembly as illustrated in FIGS. 6 and 9. Cable assemblies providing for remote operation can be either rigid as illustrated in the embodiment of FIG. 3 or flexible as illustrated in the embodiment of FIG. 4. Handle assemblies can also vary widely as illustrated in the different embodiments of FIGS. 1, 2, 4, and 5. All of the foregoing embodiments and variations thereof are believed to be within the concept of the present invention.

What is claimed is:

1. A surgical clamp, comprising:
   a semi-rigid shaft extending between a proximal end and a distal end;
   a pair of clamping jaws disposed at the distal end of the semi-rigid shaft and movable relative to each other to clamp an object between the jaws;
   a handle assembly disposed at the proximal end of the semi-rigid shaft, the handle assembly being operable at the proximal end of the semi-rigid shaft to move the jaws relative to each other at the distal end of the semi-rigid shaft to clamp the object; and the semi-rigid shaft being sufficiently flexible to be movable from a first shape into a desired, second shape, and being sufficiently rigid for maintaining the desired, second shape during operation of the handle assembly.

2. The surgical clamp recited in claim 1 wherein the shaft is malleable.

3. The surgical clamp recited in claim 1, further comprising:

a control element extending relative to the shaft and moveable by the handle assembly at the proximal end of the shaft to operate the jaws at the distal end of the shaft.

4. The surgical clamp recited in claim 3, wherein:

the shaft comprises a tube having a lumen; and the control element is disposed relative to the lumen of the tube.

5. The surgical clamp recited in claim 4, wherein the control element has properties for being placed in tension to operate the jaws.

6. The surgical clamp recited in claim 5, wherein the control element has properties for being placed in compression to operate the jaws.

7. The surgical clamp recited in claim 5, wherein the control element includes a wire.

8. The surgical clamp recited in claim 6, wherein the tube of the shaft is a first tube and the control element comprises a second tube disposed relative to thie first tube.

9. The surgical clamp recited in claim 8, wherein the second tube is disposed interiorly of the first tube.

10. The surgical clamp recited in claim 8, wherein the second tube is disposed exteriorly of the first tube.

11. The surgical clamp recited in claim 5, wherein the jaws are movable between a first position and a second position and the surgical clamp further comprises:

a spring coupled to at least one of the jaws for biasing the jaws to the first position.

12. The surgical clamp recited in claim 11, wherein the first position is a closed position.

13. A surgical clamp, comprising:

a shaft extending between a proximal end and a distal end;

a pair of clamping jaws disposed at the distal end of the shaft and movable relative to each other to clamp an object between the jaws;

a handle assembly disposed at the proximal end of the shaft, the handle assembly being operable at the proximal end of the shaft to move the jaws relative to each other at the distal end of the shaft to clamp the object; and the shaft comprising a semi-rigid bendable element extending along a first axis between the handle assembly and the jaws, the semi-rigid bendable element being sufficiently flexible to be movable from a first shape into a desired, second shape, and being sufficiently rigid for maintaining the desired, second shape during operation of the handle assembly; and a control element extending relative to the bendable element along a second axis, the control element being operable from the handle assembly at the proximal end of the shaft to move the jaws relative to each other at the distal end of the shaft.

14. The surgical clamp recited in claim 13, Awherein the first axis of the bendable element is co-axial with the second axis of the control element.

15. The surgical clamp recited in claim 14, wherein:

the bendable element includes a tube; and the control element is disposed within the tube of the bendable element.

16. The surgical clamp recited in claim 14, wherein:

the control element includes a tube; and the bendable element is disposed within the tube of the control element.

17. The surgical clamp recited in claim 13, wherein the semi-rigid element is malleable.

18. The surgical clamp recited in claim 13, wherein the semi-rigid element is corrugated.

19. The surgical clamp recited in claim 13, wherein the semi-rigid element includes a series of ball-and-socket joints.

20. A method for operating a surgical clamp, comprising the steps of:

providing a shaft having a proximal end and a distal end with a pair of clamping jaws at the distal end and movable to clamp an object during a surgical operation, and a handle assembly disposed at the proximal end to operate the jaws at the distal end during the surgical operation;

bending the shaft to a desired shape prior to operation of the clamp; and maintaining the shaft in substantially the desired shape without external force during operation of the clamp.

21. The method recited in claim 20, wherein the providing step includes the step of providing the shaft with a corrugated configuration.

22. The method recited in claim 20, wherein the providing step includes the step of providing the shaft in the form of a series of ball-and-socketjoints.

* * * * *